United States Patent [19]
Ning et al.

[11] Patent Number: 5,247,072
[45] Date of Patent: Sep. 21, 1993

[54] CARBOXYALKYL POLYSACCHARIDES HAVING IMPROVED ABSORBENT PROPERTIES AND PROCESS FOR THE PREPARATION THEREOF

[75] Inventors: Xin Ning, Appleton; Tong Sun, Neenah, both of Wis.

[73] Assignee: Kimberly-Clark Corporation, Neenah, Wis.

[21] Appl. No.: 952,216

[22] Filed: Sep. 28, 1992

Related U.S. Application Data

[63] Continuation of Ser. No. 808,086, Dec. 11, 1991, which is a continuation-in-part of Ser. No. 782,853, Oct. 25, 1991.

[51] Int. Cl.$^5$ .................. C08B 11/12; C08B 37/02
[52] U.S. Cl. ........................... 536/97; 536/98; 536/112; 536/114; 536/120
[58] Field of Search ............... 536/97, 98, 112, 114, 536/120

[56] References Cited

U.S. PATENT DOCUMENTS

| | | | |
|---|---|---|---|
| Re. 31,323 | 7/1983 | Marder et al. | 536/87 |
| 1,682,294 | 8/1928 | Lilienfeld | 524/47 |
| 1,884,629 | 10/1932 | Dreyfus | 524/47 |
| 1,938,360 | 12/1933 | Traill | 524/47 |
| 2,096,681 | 10/1937 | Lerand | 524/47 |
| 2,110,526 | 3/1938 | Lorand | 524/47 |
| 2,131,733 | 10/1938 | Haskins | 524/47 |
| 2,137,343 | 11/1938 | Maxwell | 524/47 |
| 2,159,376 | 5/1939 | Freeman et al. | 524/47 |
| 2,170,009 | 8/1939 | Clarke et al. | 524/47 |
| 2,181,264 | 11/1939 | Dreyfus | 524/47 |
| 2,236,523 | 4/1941 | Coolidge | 524/47 |
| 2,236,545 | 4/1941 | Maxwell et al. | 524/47 |
| 2,278,612 | 4/1942 | Coolings et al. | 524/47 |
| 2,486,805 | 11/1949 | Seymour et al. | 117/68 |
| 2,517,577 | 8/1950 | Klug et al. | 524/47 |
| 2,523,377 | 9/1950 | Klug | 524/47 |
| 2,524,024 | 9/1950 | Swinehart et al. | 524/47 |
| 2,639,239 | 5/1953 | Elliot | 106/197 |
| 2,680,737 | 6/1954 | Grassie et al. | 260/233 |
| 2,772,999 | 12/1956 | Masci et al. | 167/84 |
| 2,773,000 | 12/1956 | Masci et al. | 167/84 |
| 2,976,278 | 3/1961 | Paddison | 524/47 |
| 3,055,369 | 9/1962 | Graham, Jr. | 128/285 |
| 3,345,358 | 10/1967 | Inklaar | 524/47 |
| 3,347,236 | 10/1967 | Torr | 128/284 |
| 3,347,855 | 10/1967 | Nelson | 524/47 |
| 3,379,720 | 4/1968 | Reid | 536/87 |
| 3,423,167 | 1/1969 | Kuzmak et al. | 8/129 |
| 3,551,410 | 12/1970 | MacDonald et al. | 524/47 |
| 3,589,364 | 6/1971 | Dean et al. | 128/284 |
| 3,618,607 | 11/1971 | Ells et al. | 128/285 |
| 3,678,031 | 7/1972 | Schoggen | 524/47 |
| 3,723,413 | 3/1973 | Chatterjee et al. | 524/47 |
| 3,731,686 | 5/1973 | Chatterjee | 128/285 |
| 3,826,711 | 7/1974 | Schoggen et al. | 162/102 |
| 3,847,636 | 11/1974 | Smith | 106/168 |
| 3,858,585 | 1/1975 | Chatterjee | 128/290 R |
| 3,935,009 | 1/1976 | Weaver et al. | 210/43 |
| 3,936,441 | 2/1976 | Holst et al. | 524/47 |
| 3,965,091 | 6/1976 | Holst et al. | 524/47 |
| 3,971,379 | 7/1976 | Chatterjee | 128/285 |
| 3,981,100 | 9/1976 | Weaver et al. | 47/58 |
| 4,044,766 | 8/1977 | Kaczmarzyk et al. | 128/285 |
| 4,117,222 | 9/1978 | Holst et al. | 536/50 |
| 4,127,944 | 12/1978 | Giacobello | 34/9 |

(List continued on next page.)

FOREIGN PATENT DOCUMENTS

| | | |
|---|---|---|
| 731146 | 3/1966 | Canada . |
| 0319865 | 6/1989 | European Pat. Off. . |
| 1550614 | 8/1979 | United Kingdom . |
| 2104932 | 3/1983 | United Kingdom . |
| WO9102552 | 3/1991 | World Int. Prop. O. . |

*Primary Examiner*—Nathan M. Nutter
*Attorney, Agent, or Firm*—Thomas J. Mielke

[57] ABSTRACT

Disclosed is a method for producing a water-swellable, generally water-insoluble, carboxyalkyl polysaccharide having improved absorption properties. The method involves forming a solution of carboxyalkyl polysaccharide and water, recovering the carboxyalkyl polysaccharide from the solution and heat-treating said recovered carboxyalkyl polysaccharide. Also, described is a carboxyalkyl polysaccharide having improved absorption properties.

34 Claims, 10 Drawing Sheets

U.S. PATENT DOCUMENTS

| | | | |
|---|---|---|---|
| 4,155,888 | 5/1979 | Mooth | 527/301 |
| 4,200,736 | 4/1980 | Shinohara et al. | 536/87 |
| 4,252,761 | 2/1981 | Schoggen et al. | 264/120 |
| 4,340,731 | 7/1982 | Colombo et al. | 536/98 |
| 4,454,055 | 6/1984 | Richman et al. | 252/194 |
| 4,483,950 | 11/1984 | Fanta et al. | 524/48 |
| 4,650,716 | 3/1987 | Gelman | 428/402 |
| 4,683,298 | 7/1987 | Yalpani | 536/45 |
| 4,689,408 | 8/1987 | Gelman et al. | 536/87 |
| 4,990,551 | 2/1991 | Haubl et al. | 524/30 |
| 5,001,232 | 3/1991 | Herzog et al. | 536/90 |
| 5,005,771 | 4/1991 | Pieh et al. | 241/23 |
| 5,079,354 | 1/1992 | Gross et al. | 536/111 |

□ = Sample No.'s 18, 20, 21, 22, 23, 24, 25, 26, 27
◆ = Sample No.'s 20, 22, 24, 26, 27

CARBOXYALKYL POLYSACCHARIDES HAVING IMPROVED ABSORBENT PROPERTIES AND PROCESS FOR THE PREPARATION THEREOF

This is a continuation application of copending application Ser. No. 07/808,086 filed on Dec. 11, 1991, which in turn is a continuation-in-part application of Ser. No. 07/782,853 filed on Oct. 25, 1991.

BACKGROUND OF THE INVENTION

1. Field of the Invention

The present invention relates to carboxyalkyl polysaccharides having improved absorbent properties. Specifically, the present invention relates to carboxyalkyl polysaccharides having the ability to absorb liquid while under a load and a process for the preparation thereof.

2. Description of the Related Art

The use of absorbent materials, commonly known as superabsorbents, in disposable absorbent personal care products is known. Such absorbent materials are generally employed in absorbent products such as diapers, training pants, adult incontinence products, feminine care products, and the like, in order to increase the absorbent capacity of such products while reducing their overall bulk. Such absorbent materials are generally present in absorbent products in a fibrous matrix, such as a matrix of wood pulp fluff. A matrix of wood pulp fluff generally has an absorbent capacity of about 6 grams of liquid per gram of fluff. The absorbent materials described above generally have an absorbent capacity of at least about 10, preferably of about 20, and often of up to 100 times their weight in water. Clearly, incorporation of such absorbent materials in personal care products can reduce the overall bulk while increasing the absorbent capacity of such products.

A wide variety of materials have been described for use as absorbent materials in such personal care products. Such materials include natural-based materials such as agar, pectin, gums, carboxyalkyl starch, carboxyalkyl cellulose, and the like, as well as synthetic materials such as polyacrylates, polyacrylamides, hydrolyzed polyacrylonitrile, and the like. While the natural-based, absorbent materials are known for use in personal care products, they have not gained wide usage in such products. The natural-based, absorbent materials have not gained wide usage in personal care products, at least in part, because their absorbent properties are inferior compared to the synthetic absorbent materials such as the polyacrylates. Specifically, many of the natural-based materials tend to form soft, gelatinous masses when swollen with a liquid. When employed in absorbent products, the presence of such soft gelatinous masses tends to prevent the transport of liquid within the fibrous matrix in which the absorbent materials are incorporated. This phenomenon is known as gel-blocking. Once gel-blocking occurs, subsequent insults of liquid cannot be efficiently absorbed by the product, and the product tends to leak. Further, many of the natural-based materials exhibit poor absorption properties, particularly when subjected to external pressures.

In contrast, the synthetic, absorbent materials are often capable of absorbing large quantities of liquid while maintaining a generally stiff, non-gelatinous character. Accordingly, the synthetic, absorbent materials can be incorporated in absorbent products while minimizing the likelihood of gel-blocking.

Carboxyalkyl cellulose materials and other carboxyalkyl polysaccharides are known in the art. As a general rule, carboxyalkyl cellulose materials are formed from a cellulosic material which has been treated with carboxyalkylating reactants such as a chloroalkanoic acid, preferably monochloroacetic acid, and an alkali, such as sodium hydroxide, optionally, in the presence of an alcohol. Such a process is described, for example, in U.S. Pat. No. 3,723,413, issued Mar. 27, 1973, to Chatterjee et al. Such carboxyalkyl celluloses are generally water-soluble. Various methods of rendering such water-soluble carboxyalkyl celluloses water-insoluble are known.

U.S. Pat. No. 2,639,239 issued May 19, 1953, to Elliott describes a process in which a commercially available water-soluble, alkali-metal salt of carboxymethyl cellulose having a degree of substitution of from about 0.5 to about 1 is subjected to a thermal treatment for up to 10 hours which renders such water-soluble carboxymethyl cellulose capable of forming highly swollen gel particles.

Similarly, U.S. Pat. No. 3,723,413, discussed above, describes the heat treatment of a carboxyalkyl cellulose in the presence of remaining carboxyalkylating reactants and by-products, such that the carboxyalkyl cellulose becomes water-insoluble and possessed of desirable liquid absorptive and retentive properties and characteristics.

U.S. Pat. No. 3,379,720 issued Apr. 23, 1968, to Reid describes a process of preparing modified polysaccharides such as ethers and esters of cellulose comprising slurrying a water-soluble polysaccharide in any inert medium, acidifying said polysaccharide, removing excess acid from the acidified polysaccharide, drying same and heat-curing.

U.S. Pat. No. 4,689,408 issued Aug. 25, 1987, to Gelman et al. describes a method of preparing salts of carboxymethyl cellulose. The method involves treating a carboxymethyl cellulose with water, adding a nonsolvent for the carboxymethyl cellulose, and recovering the carboxymethyl cellulose. The carboxymethyl cellulose is said to have an absorbency of at least 25 grams of liquid per gram of carboxymethyl cellulose.

Unfortunately, the known carboxyalkyl polysaccharide materials do not possess absorptive properties comparable to many of the synthetic, highly absorptive materials. This has prevented widespread use of such carboxyalkyl polysaccharides in absorbent personal care products.

SUMMARY OF THE INVENTION

It is desirable to develop and produce a natural-based, highly absorbent material having absorptive properties similar to the synthetic, highly absorptive materials and thus suitable for use in personal care absorbent products.

The present invention concerns a method for producing a water-swellable, water-insoluble carboxyalkyl polysaccharide. The method comprises the steps of forming a solution comprising a water-soluble carboxyalkyl polysaccharide and water. The carboxyalkyl polysaccharide has an average degree of substitution of from about 0.3 to about 1.5. The carboxyalkyl polysaccharide is recovered from said solution and heat-treated at a temperature and for a time sufficient to crosslink the carboxyalkyl polysaccharide.

The present invention further concerns a water-swellable, generally water-insoluble carboxyalkyl polysaccharide. The carboxyalkyl polysaccharide is characterized in that it has an average degree of substitution of from about 0.3 to about 1.5, that it has an Absorbency Under Load of at least about 17 and a Free-Swell Capacity of at least about 20 grams per gram.

DETAILED DESCRIPTION OF THE PREFERRED EMBODIMENT

Figure 1:
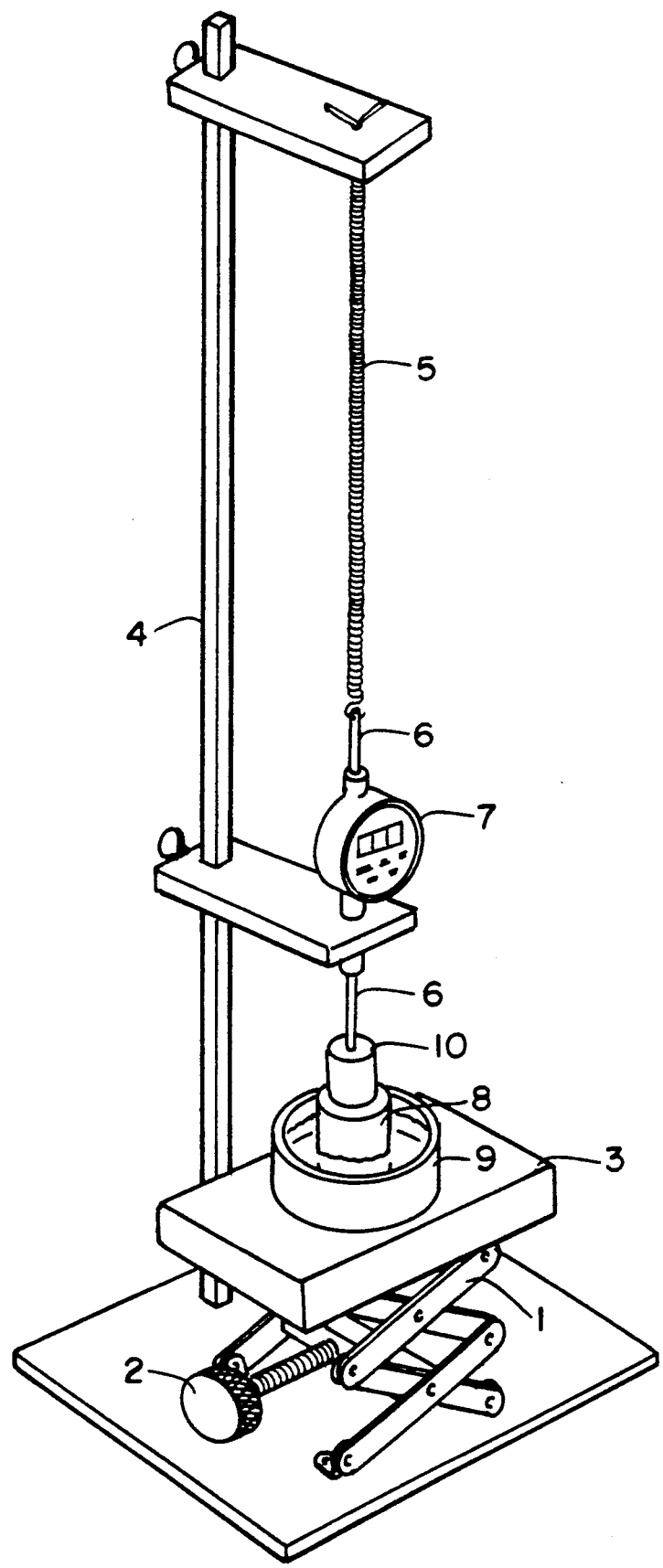
FIG. 1 illustrates the apparatus for determining the Absorbency Under Load values of an absorbent material.

In one aspect, the present invention concerns a method for producing a water-swellable, water-insoluble carboxyalkyl polysaccharide. The method comprises the steps of forming a solution comprising carboxyalkyl polysaccharide and water. The carboxyalkyl polysaccharide is recovered from the solution and heat-treated for a time and at a temperature sufficient to crosslink the carboxyalkyl polysaccharide.

Suitable carboxyalkyl polysaccharides for use in the present invention include carboxyalkyl cellulose such as carboxymethyl cellulose, carboxyethyl cellulose, carboxyalkyl carageenan, carboxyalkyl agar, carboxyalkyl gellan gum, and the like, and mixtures thereof. The preferred carboxyalkyl polysaccharide is a carboxyalkyl cellulose with the preferred carboxyalkyl cellulose being carboxymethyl cellulose. While any carboxyalkyl polysaccharide is believed suitable for use in the present invention, carboxyalkyl cellulose is preferred. Accordingly, the preferred embodiments discussed below will be described in the context of using carboxyalkyl cellulose as the carboxyalkyl polysaccharide. However, it is to be understood that other suitable carboxyalkyl polysaccharides can be used.

Methods of making carboxyalkyl cellulose are known to those skilled in the art. Suitably, a cellulosic material such as wood pulp fluff, cotton, cotton linters, and the like are provided. The cellulosic material may be in the form of fibers or of fibers which have been comminuted to particulate form. The cellulosic material is dispersed in an inert solvent such as an alcohol and carboxyalkylating reagents added to the dispersion. Carboxyalkylating reagents generally comprise a chloroalkanoic acid such as monochloroacetic acid and sodium hydroxide.

It is to be understood that it may be possible to perform the carboxyalkylation of the starting polysaccharide in such a manner that the solution of carboxyalkyl cellulose and water is formed directly. That is, the carboxyalkylation process may be performed in an aqueous medium such that, upon formation of the carboxyalkyl cellulose, it is solubilized in the water. In this manner, no recovery step is necessary between formation of the carboxyalkyl cellulose and the formation of the solution of carboxyalkyl cellulose and water.

The carboxyalkyl celluloses suitable for use in the present invention generally have an average degree of substitution from about 0.3 to about 1.5, preferably from about 0.4 to about 1.2. The degree of substitution refers to the average number of carboxyl groups present on the anhydroglucose unit of the cellulosic material. When the carboxyalkyl celluloses have an average degree of substitution within the range of from about 0.3 to about 1.5, the carboxyalkyl cellulose is generally water-soluble.

As used herein, a carboxyalkyl cellulose will be considered to be water-soluble when it either dissolves in water to form a true solution, or swells in water to a large extent even though a true solution may not be formed.

Carboxyalkyl cellulose is available in a wide range of molecular weights. Carboxyalkyl cellulose having a relatively high molecular weight is desired for use in the present invention. It is generally most convenient to express the molecular weight of a carboxyalkyl cellulose in terms of its viscosity in a 2.0 weight percent aqueous solution. Carboxymethyl celluloses suitable for use in the present invention will generally have a viscosity in a 2.0 weight percent aqueous solution of from about 50 centipoise to about 80,000 centipoise, preferably from about 2,000 centipoise to about 80,000 centipoise, and most preferably from about 20,000 centipoise to about 80,000 centipoise.

Suitable carboxyalkyl celluloses are commercially available from numerous vendors. Exemplary of a commercially available carboxyalkyl cellulose is carboxymethyl cellulose, commercially available from Aqualon Company under the trade designation Aqualon TM or Blanose TM Cellulose Gum.

The solution of carboxyalkyl cellulose and water suitably comprises from about 0.01 to about 90 weight percent, beneficially from about 0.01 to about 30 weight percent, and preferably from about 2 to about 25 weight percent of carboxyalkyl cellulose based on total solution weight. The carboxyalkyl cellulose is suitably dissolved in a solvent comprising at least about 30 weight percent water, beneficially about 50 weight percent water, preferably about 75 weight percent water, and most preferably about 100 weight percent water. When a co-solvent is employed with the water, other suitable solvents include methanol, ethanol, and acetone.

The solution of carboxyalkyl cellulose and water and the recovered carboxyalkyl cellulose may be acidic, neutral, or slightly basic. As used herein, acidity will be stated in terms of the degree of molar acidification (DA). The degree of molar acidification is defined as the number of free-acid, carboxyl groups divided by the total number of carboxyl groups, either free-acid or salt-form. The degree of molar acidification is suitably less than 0.07, preferably less than about 0.05, assuming use of an essentially completely neutralized carboxyalkyl cellulose having few free acid groups and little, if any, residual base. The solution of carboxyalkyl cellulose and water can be acidified by the addition of an aqueous solution of an inorganic acid such as hydrochloric acid, nitric acid, etc. or an aqueous solution of an organic acid, such as acetic acid, or the like.

If it is desired to provide the solution of carboxyalkyl cellulose and water with a basic pH, a base such as an aqueous solution of sodium hydroxide, potassium hydroxide, ammonia, or the like can be added to the solution.

The solution of carboxyalkyl cellulose and water will suitably have a pH within the range of from about 5.0 to about 11.0, beneficially from about 6.0 to about 10.0, and preferably from about 6.5 to about 9. The recovered carboxyalkyl cellulose will generally have the same pH as the solution. However, Applicants have noted that when the carboxyalkyl cellulose is recovered by evaporative drying, the evaporative drying step tends to lower the pH of the carboxyalkyl cellulose solution if it is initially basic.

When the carboxyalkyl cellulose of the present invention is intended for use in personal care products such as diapers, training pants, feminine care products, and the like, it is generally desired that the carboxyalkyl cellulose have a generally neutral character. For this reason, it is generally preferred that the solution of carboxyalkyl cellulose and water be formed with a generally neutral pH. Alternatively, if the solution of carboxyalkyl cellulose and water is formed with an acidic or basic pH, the recovered carboxyalkyl cellulose may be neutralized. For example, if the solution is acidic, the recovered carboxyalkyl cellulose will be acidic. The recovered carboxyalkyl cellulose may be neutralized, for example, by contacting with a gaseous base such as ammonia.

The solution of carboxyalkyl cellulose and water can be formed at any temperature at which the carboxyalkyl cellulose is soluble in the water. Generally, such temperatures will be within the range of from about 10° C. to about 100° C. As a general rule, it is preferred to form the solution of carboxyalkyl cellulose with agitation. After forming the solution of carboxyalkyl cellulose and water, the carboxyalkyl cellulose is recovered from the solution. Any method of recovering the carboxyalkyl cellulose from the solution, without unacceptably deteriorating the absorption characteristics of the carboxyalkyl cellulose, is suitable for use in the present invention. Examples of such methods include evaporative drying, freeze drying, precipitation, critical point drying, and the like.

As a general rule, the carboxyalkyl cellulose can be recovered by evaporative drying at a temperature within the range from of about 10° C. to about 100° C., preferably from about 50° C. to about 80° C. Naturally, higher temperatures can be employed if the solution is placed under pressure. Lower temperatures can be employed if the solution is placed under a vacuum.

Other methods of recovery include precipitation in which a precipitating agent, such as methanol, ethanol or acetone is added to the solution of carboxyalkyl cellulose and water to precipitate the carboxyalkyl cellulose out of solution. The carboxyalkyl cellulose can then be recovered by filtration. If precipitation is used to recover the carboxyalkyl cellulose, it may be desirable to wash the recovered carboxyalkyl cellulose to remove the precipitating agent. Depending on the form in which the carboxyalkyl cellulose is recovered, it may be necessary or desirable to alter the form of the carboxyalkyl cellulose. For example, if evaporative drying is employed, the carboxyalkyl cellulose may be recovered in the form of a film or sheet. It may be desirable to comminute the film or sheet material into particles or flakes of material.

The form of the carboxyalkyl cellulose desired will depend to a large extent on the use for which it is intended. When the carboxyalkyl cellulose is intended for use in absorbent personal care products, it is generally desired that the carboxyalkyl cellulose be in the form of a discrete particle, fiber or flake. When in the form of a particle, it is generally desired that the particle have a maximum cross-sectional diameter within the range from about 50 micrometers to about 2,000 micrometers, preferably within the range from about 100 micrometers to about 1,000 micrometers, most preferably within the range from about 300 micrometers to about 600 micrometers.

The recovered carboxyalkyl cellulose is then heat-treated at an elevated temperature to crosslink the carboxyalkyl cellulose. As a general rule, any combination of temperature and time which achieves a desired degree of crosslinking, without undesirable damage to the carboxyalkyl cellulose, is suitable for use in the present invention. As a general rule, the carboxyalkyl cellulose will be heat-treated at a temperature within the range from about 100° C. to about 250° C., beneficially from about 120° C. to about 200° C., and preferably from about 30° C. to about 170° C. The higher the temperature employed, the shorter the period of time necessary to achieve the desired degree of crosslinking. Generally, the heat-treating process will extend over a time period within the range of from about 1 minute to about 600 minutes, beneficially from about 1 minute to about 120 minutes, and preferably from about 5 minutes to about 60 minutes.

Applicants have discovered that, by providing the solution of carboxyalkyl cellulose and water with an acidic character, the time necessary to effect the heat-treatment can be shortened. Providing the solution of carboxyalkyl cellulose and water with a slightly basic character tends to lengthen the time of the heat-treating process, at a given temperature, compared to a slightly acidic or neutral solution of carboxyalkyl cellulose and water. Nonetheless, similar general absorptive properties can be achieved with either an acidic, neutral, or slightly basic carboxyalkyl cellulose. In some instances, it may be desired to provide the solution of carboxyalkyl cellulose and the recovered carboxyalkyl cellulose with an acidic character in order to lower the temperature or shorten the time of the heat treatment. In this instance, the carboxyalkyl cellulose is desirably neutralized after the heat-treatment step.

The heat-treating process causes the carboxyalkyl cellulose to cross link and become generally water-insoluble. The heat-treating process desirably produces a carboxyalkyl cellulose having the ability to absorb a liquid while the carboxyalkyl cellulose is under a load. Synthetic polymeric materials, such as polyacrylates, having a generally high ability to absorb while under a load have been found to minimize the occurrence of gel-blocking when incorporated in absorbent products.

The method by which the Absorbency Under Load is determined is set forth below in connection with the examples. The Absorbency Under Load values determined as set forth below and reported herein refer to the amount, in grams, of an aqueous solution containing 0.9 weight percent sodium chloride a gram of the carboxyalkyl cellulose (carboxyalkyl polysaccharide) can absorb in 60 minutes under a load of about 0.3 pounds per square inch. As a general rule, it is desired that the carboxyalkyl cellulose of the present invention have an Absorbency Under Load (AUL) of at least about 17, beneficially of at least about 20, most beneficially of at least about 24, and preferably of at least about 27 grams per gram.

Further, the carboxyalkyl cellulose of the present invention suitably has a Free-Swell Capacity of at least about 20 grams, preferably of at least about 30 grams, and most preferably of at least about 35 grams. Free-Swell Capacity refers to the amount, in grams, of an aqueous solution containing 0.9 weight percent sodium chloride the carboxyalkyl cellulose can absorb in 60 minutes under no load. The exact procedure by which the Free-Swell Capacity is determined is set forth below in connection with the examples.

Any combination of time and temperature which produces a crosslinked carboxyalkyl cellulose having the described Absorbency Under Load and Free-Swell capacity is preferred for use in the present invention. Applicants have found that there is generally an optimum combination of time and temperature at which to crosslink and optimize the Absorbency Under Load and Free-Swell Capacity of a particular carboxyalkyl cellulose material. If too little crosslinking occurs, the carboxyalkyl cellulose may possess a high Free-Swell Capacity but a relatively low Absorbency Under Load. If too much crosslinking occurs, the carboxyalkyl cellulose may have a relatively low Free-Swell Capacity and a relatively low Absorbency Under Load due to the inability of the carboxyalkyl cellulose to absorb much liquid.

Applicants have discovered that solubilizing the carboxyalkyl cellulose in an aqueous solution and recovering prior to crosslinking produces a carboxyalkyl cellulose suitable for further crosslinking into materials having improved absorption properties. For example, a standard carboxymethyl cellulose heat-treated at 150° C. for 60 minutes has an Absorbency Under Load of 6.4 grams and remains water soluble. When the same carboxymethyl cellulose is solubilized in water, recovered by evaporative drying and heat-treated at 150° C. for 60 minutes, the carboxymethyl cellulose has an Absorbency Under Load of 24.8.

Applicants hypothesize that the solubilization may allow a molecular rearrangement of the carboxyalkyl cellulose which produces a more uniform distribution of the carboxyl groups and hydroxyl groups within the carboxyalkyl cellulose material. The more uniform distribution of the carboxyl groups within the carboxyalkyl cellulose may result in a more uniform crosslinking as a result of the heat-treatment step.

Applicants are uncertain as to whether or not the crosslinking which occurs is a chemical crosslinking, a physical crosslinking caused by the formation of crystal structures, or a combination of chemical and physical crosslinking. The exact cause of the improved absorbent properties achieved by the method of the present invention is not important so long as the improved absorbent properties are achieved.

In another aspect, the present invention relates to a water-swellable, generally water-insoluble carboxyalkyl polysaccharide characterized in that it has an average degree of substitution of from about 0.3 to about 1.5 and has an Absorbency Under Load value of at least about 17 and a Free-Swell Capacity of at least about 20 grams per gram. Such a carboxyalkyl polysaccharide is suitably formed by the method described above. Nonetheless, the described method is not intended to be the exclusive method by which such a carboxyalkyl polysaccharide can be formed.

As described above, the carboxyalkyl polysaccharide is suitably a carboxyalkyl cellulose such as carboxymethyl cellulose, carboxymethyl cellulose, or the like. The carboxyalkyl cellulose has an Absorbency Under Load value of at least 17, beneficially of at least about 20, preferably of at least 24, and most preferably of at least about 27. The carboxyalkyl cellulose has a Free-Swell Capacity of at least about 20, beneficially of at least about 30, and preferably of at least 35.

The carboxyalkyl polysaccharides of the present invention are suitable for use in personal care products such as diapers, training pants, feminine care products, adult incontinent products, wound dressings, and the like.

TEST METHODS

Absorbency Under Load

The Absorbency Under Load (AUL) is a test which measures the ability of an absorbent material to absorb a liquid (0.9 weight percent solution of sodium chloride in distilled water) while under an applied load or restraining force.

Referring to FIG. 1, the apparatus and method for determining AUL will be described. Shown is a perspective view of the apparatus in position during a test. Shown is a laboratory jack 1 having an adjustable knob 2 for raising and lowering the platform 3. A laboratory stand 4 supports a spring 5 connected to a modified thickness meter probe 6, which passes through the housing 7 of the meter, which is rigidly supported by the laboratory stand. A plastic sample cup 8, which contains the superabsorbent material sample to be tested, has a liquid-permeable bottom and rests within a Petri dish 9, which contains the saline solution to be absorbed. A weight 10 rests on top of a spacer disc (not visible) resting on top of the superabsorbent material sample (not visible).

The sample cup consists of a plastic cylinder having a 1 inch inside diameter and an outside diameter of 1.25 inch. The bottom of the sample cup is formed by adhering a 100 mesh metal screen having 150 micron opening to the end of the cylinder by heating the screen above the melting point of the plastic and pressing the plastic cylinder against the hot screen to melt the plastic and bond the screen to the plastic cylinder.

The modified thickness meter used to measure the expansion of the sample while absorbing the saline solution is a Mitutoyo Digimatic Indicator, IDC Series 543, Model 543-180, having a range of 0–0.5 inch and an accuracy of 0.00005 inch (Mitutoyo Corporation, 31-19, Shiba 5-chome, Minato-ku, Tokyo 108, Japan). As supplied from Mitutoyo Corporation, the thickness meter contains a spring attached to the probe within the meter housing. This spring is removed to provide a free falling probe, which has a downward force of about 27 grams. In addition, the cap over the top of the probe located on the top of the meter housing is also removed to enable attachment of the probe to the suspension spring 5 (available from McMaster-Carr Supply Co., Chicago, Ill., Item No. 9640K41), which serves to counter or reduce the downward force of the probe to about 1 gram, ±0.5 gram. A wire hook can be glued to the top of the probe for attachment to the suspension spring. The bottom tip of the probe is also provided with an extension needle (Mitutoyo Corporation, Part No. 131279) to enable the probe to be inserted into the sample cup.

To carry out the test, a 0.160 gram sample of the absorbent material, which has been sieved to a particle size between 300 and 600 microns, is placed into the sample cup. The sample is then covered with a plastic spacer disc, weighing 4.4 grams, which is slightly smaller than the inside diameter of the sample cup and serves to protect the sample from being disturbed during the test. The 100 grams weight is then placed on top of the spacer disc, thereby applying a load of 0.3 pounds per square inch. The sample cup is placed in the Petri dish on the platform of the laboratory jack raised up until it contacts the tip of the probe. The meter is zeroed. A sufficient amount of saline solution is added to the Petri dish (50–100 milliliters) to begin the test. The distance the weight is raised by the expanding sample as it absorbs the saline solution is measured by the probe. This distance, multiplied by the cross-sectional area inside the sample cup, is a measure of the expansion volume of the sample due to absorption. Factoring in the density of the saline solution and the weight of the sample, the amount of saline solution absorbed is readily calculated. The weight of saline solution absorbed after 60 minutes is the AUL value, expressed as grams saline solution absorbed per gram of absorbent. If desired, the readings of the modified thickness meter can be continuously input to a computer (Mitutoyo Digimatic Miniprocessor DP-2 DX) to make the calculations and provide AUL readings. As a cross-check, the AUL can also be determined by determining the weight difference between the sample cup before and after the test, the weight difference being the amount of solution absorbed by the sample.

Free-Swell Capacity

The Free-Swell Capacity for a given absorbent material is determined in the same manner as the Absorbency Under Load, with the exception that the 100 gram weight is not placed on top of the spacer disc. The Free-Swell Capacity is reported as the weight of the saline solution absorbed after 60 minutes, expressed as grams of saline absorbed per gram of absorbent.

EXAMPLES

Example 1

A sodium carboxymethyl cellulose commercially available from the Aqualon Company under the trade designation Aqualon ™ Cellulose Gum CMC-7HCF or CMC-7H4F is provided. The carboxymethyl cellulose has an average degree of substitution of 0.7. CMC-7H4F has a slightly higher molecular weight than the CMC-7HCF. The carboxymethyl cellulose is dissolved in distilled water to form a solution containing 2 weight percent carboxymethyl cellulose based on total solution weight. The solution is then either left at a neutral pH, slightly acidified through the addition of hydrochloric acid (0.1 molar aqueous solution) or made basic by the addition of sodium hydroxide (0.1 molar aqueous solution). The carboxymethyl cellulose is recovered from the solution by evaporative drying at 80° C. in a Blue M air-convection oven. After drying, the recovered carboxymethyl cellulose is ground into granules in a blender and heat-treated at various times and temperatures in an oven. Various combinations of temperature, time, and solution pH are made, and the physical properties of the resultant carboxymethyl cellulose determined. The exact process conditions and the physical properties of the resultant carboxymethyl cellulose are set forth in Table 1. Sample Nos. 1–38 employ the CMC-7HCF while Samples Nos. 39–45 employ the CMC-7H4F.

TABLE 1

| Sample No. | pH (DA)[1] | Treatment Temp (°C.) | Treatment Time (min) | AUL[2] (g/g) | FSC[3] (g/g) |
| --- | --- | --- | --- | --- | --- |
| 1* | 6.08 (3) | N/A | N/A | 9.7 | |
| 2 | 6.08 (3) | 140 | 5 | 16.9 | |
| 3 | 6.08 (3) | 140 | 8 | 15.5 | |
| 4 | 6.08 (3) | 140 | 10 | 14.9 | |
| 5 | 6.08 (3) | 140 | 20 | 12.6 | |
| 6 | 6.08 (3) | 140 | 30 | 10.8 | |
| 7* | 6.44 (0.5) | N/A | N/A | 6.4 | |
| 8 | 6.44 (0.5) | 120 | 60 | 19.3 | |
| 9 | 6.44 (0.5) | 140 | 10 | 16.1 | |
| 10 | 6.44 (0.5) | 140 | 20 | 20.0 | |
| 11 | 6.44 (0.5) | 140 | 30 | 20.0 | |
| 12 | 6.44 (0.5) | 140 | 40 | 18.0 | |
| 13 | 6.44 (0.5) | 140 | 50 | 16.8 | |
| 14 | 6.44 (0.5) | 150 | 10 | 17.8 | |
| 15 | 6.44 (0.5) | 150 | 15 | 20.0 | |
| 16 | 6.44 (0.5) | 150 | 20 | 19.9 | |
| 17 | 6.44 (0.5) | 150 | 30 | 15.2 | |
| 18* | 7.4 (0) | N/A | N/A | 7.1 | |
| 19 | 7.4 (0) | 130 | 90 | 22.2 | |
| 20 | 7.4 (0) | 150 | 30 | 21.4 | 46.5 |
| 21 | 7.4 (0) | 150 | 40 | 25.3 | |
| 22 | 7.4 (0) | 150 | 45 | 27.1 | 44.6 |
| 23 | 7.4 (0) | 150 | 50 | 26.1 | |
| 24 | 7.4 (0) | 150 | 60 | 24.8 | 43.7 |
| 25 | 7.4 (0) | 150 | 75 | 23.7 | |
| 26 | 7.4 (0) | 150 | 90 | 21.6 | 34.8 |
| 27 | 7.4 (0) | 150 | 120 | 19.2 | 29.6 |
| 28* | 8.92 | N/A | N/A | 7.0 | |
| 29 | 8.92 | 150 | 40 | 17.1 | |
| 30 | 8.92 | 150 | 80 | 21.8 | |
| 31 | 8.92 | 150 | 100 | 20.9 | |
| 32 | 8.92 | 150 | 120 | 21.6 | |
| 33 | 8.92 | 150 | 150 | 18.6 | |
| 34* | 10.72 | N/A | N/A | 6.6 | |
| 35 | 10.72 | 150 | 50 | 11.6 | |
| 36 | 10.72 | 150 | 100 | 19.3 | |
| 37 | 10.72 | 150 | 150 | 20.4 | |
| 38 | 10.72 | 150 | 200 | 15.9 | |
| 39* | 0 | N/A | N/A | 8.1 | |
| 40 | 0 | 150 | 8 | 27.4 | |
| 41 | 0 | 150 | 10 | 27.7 | |
| 42 | 0 | 150 | 12 | 27.8 | |
| 43 | 0 | 150 | 15 | 27.0 | |
| 44 | 0 | 150 | 20 | 27.4 | |
| 45 | 0 | 150 | 60 | 18.5 | |

N/A Not applicable
*Not an example of the present invention
[1]pH of the solution of carboxymethyl cellulose and water prior to recovery (Degree of Molar Acidification)
[2]Absorbency Under Load in grams absorbed aqueous saline solution (0.9 weight percent) per gram of carboxymethyl cellulose under a load of 0.3 psi.
[3]Free Swell Capacity in grams absorbed aqueous saline solution (0.9 weight percent) per gram of carboxymethyl cellulose.

EXAMPLE 2

Example 1 is repeated with the exception that a sodium carboxymethyl cellulose commercially available from the Aqualon Company under the trade designation Aqualon ™ Cellulose Gum CMC-9H4 is employed. The carboxymethyl cellulose has an average degree of substitution of 0.9. Again, the exact process conditions and physical properties of the resultant carboxymethyl cellulose are set forth in Table 2.

TABLE 2

| Sample No. | DA (mol %)[1] | Treatment Temp (°C.) | Treatment Time (min) | AUL[2] (g/g) | FSC[3] (g/g) |
|---|---|---|---|---|---|
| 46 | 3 | 150 | 30 | 10.5 | |
| 47* | 0.5 | N/A | N/A | 7.2 | |
| 48 | 0.5 | 150 | 5 | 17.9 | |
| 49 | 0.5 | 150 | 8 | 22 | |
| 50 | 0.5 | 150 | 10 | 22.3 | |
| 51 | 0.5 | 150 | 15 | 20.5 | |
| 52 | 0.5 | 150 | 20 | 18.3 | |
| 53 | 0.5 | 150 | 30 | 16 | |
| 54* | 0.1 | N/A | N/A | 6.9 | |
| 55 | 0.1 | 150 | 10 | 10.7 | |
| 56 | 0.1 | 150 | 20 | 22.1 | |
| 57 | 0.1 | 150 | 30 | 22.2 | |
| 58 | 0.1 | 150 | 40 | 20.4 | |
| 59 | 0.1 | 150 | 60 | 18.8 | |
| 60* | 0 | N/A | N/A | 7.4 | |
| 61 | 0 | 130 | 60 | 8.7 | |
| 62 | 0 | 130 | 90 | 15.8 | |
| 63 | 0 | 130 | 120 | 20.3 | |
| 64 | 0 | 130 | 150 | 22.8 | |
| 65 | 0 | N/A | N/A | 7.4 | |
| 66 | 0 | 170 | 10 | 19.8 | |
| 67 | 0 | 170 | 20 | 13.3 | |
| 68 | 0 | 170 | 30 | 10.5 | |

N/A = Not Applicable
*Not an example of the present invention
[1]Degree of Molar Acidification
[2]Absorbency Under Load in grams absorbed aqueous saline solution (0.9 weight percent) per gram of carboxymethyl cellulose under a load of 0.3 psi.
[3]Free Swell Capacity in grams absorbed aqueous saline solution (0.9 weight percent) per gram of carboxymethyl cellulose.

EXAMPLE 3

Example 2 is repeated with the exception that the carboxymethyl cellulose is recovered and comminuted to form both granules and flakes. The carboxymethyl cellulose is then heat-treated at 150° C. for various times to determine the effect of geometry on the heat-treatment process. The results are set forth in Table 3. Samples 69–73 are in granular form. Samples 74–80 are in the form of flakes.

TABLE 3

| Sample No. | DA (mol %)[1] | Treatment Temp (°C.) | Treatment Time (min) | AUL[2] (g/g) |
|---|---|---|---|---|
| 69* | 0 | N/A | N/A | 7.4 |
| 70 | 0 | 150 | 20 | 19 |
| 71 | 0 | 150 | 30 | 24 |
| 72 | 0 | 150 | 40 | 24.5 |
| 73 | 0 | 150 | 50 | 22.4 |
| 74* | 0 | N/A | N/A | 7.4 |
| 75 | 0 | 150 | 10 | 9.8 |
| 76 | 0 | 150 | 15 | 15.8 |
| 77 | 0 | 150 | 20 | 25 |
| 78 | 0 | 150 | 30 | 23 |
| 79 | 0 | 150 | 45 | 20.8 |
| 80 | 0 | 150 | 60 | 18.4 |

N/A = Not Applicable
*Not an example of the present invention
[1]Degree of Molar Acidification
[2]Absorbency Under Load in grams absorbed aqueous saline solution (0.9 weight percent) per gram of carboxymethyl cellulose under a load of 0.3 psi.

EXAMPLE 4

Example 2 is repeated with the exception that the carboxymethyl cellulose is dissolved in distilled water to form a solution containing 23 weight percent carboxymethyl cellulose based on total solution weight. The recovered carboxymethyl cellulose is heat-treated in the form of granules at 150° C. for various time periods. The physical properties of the resultant polymer are set forth in Table 4.

TABLE 4

| Sample No. | DA (mol %)[1] | Treatment Temp (°C.) | Treatment Time (min) | AUL[2] (g/g) |
|---|---|---|---|---|
| 81* | 0 | N/A | N/A | 7.3 |
| 82 | 0 | 150 | 20 | 22 |
| 83 | 0 | 150 | 30 | 22.2 |
| 84 | 0 | 150 | 40 | 20.5 |

N/A = Not Applicable
*Not an example of the present invention
[1]Degree of Molar Acidification
[2]Absorbency Under Load in grams absorbed aqueous saline solution (0.9 weight percent) per gram of carboxymethyl cellulose under a load of 0.3 psi.

Control samples of the carboxymethyl cellulose of Example 1 and Example 2 in which the carboxymethyl cellulose is subjected to a heat-treatment process without having been dissolved in an aqueous solution and recovered were performed. Again, the exact process conditions of the heat-treatment step and the physical properties of the resultant polymer are set forth in Table 5. Both control samples remain water soluble even after the heat-treatment step.

TABLE 5

| Sample No. | Treatment Temp (°C.) | Treatment Time (min) | AUL (g/g) |
|---|---|---|---|
| 85* | 150 | 15 | 6.8 |
| 86* | 150 | 60 | 6.4 |

*Not an example of the present invention

Figure 2:
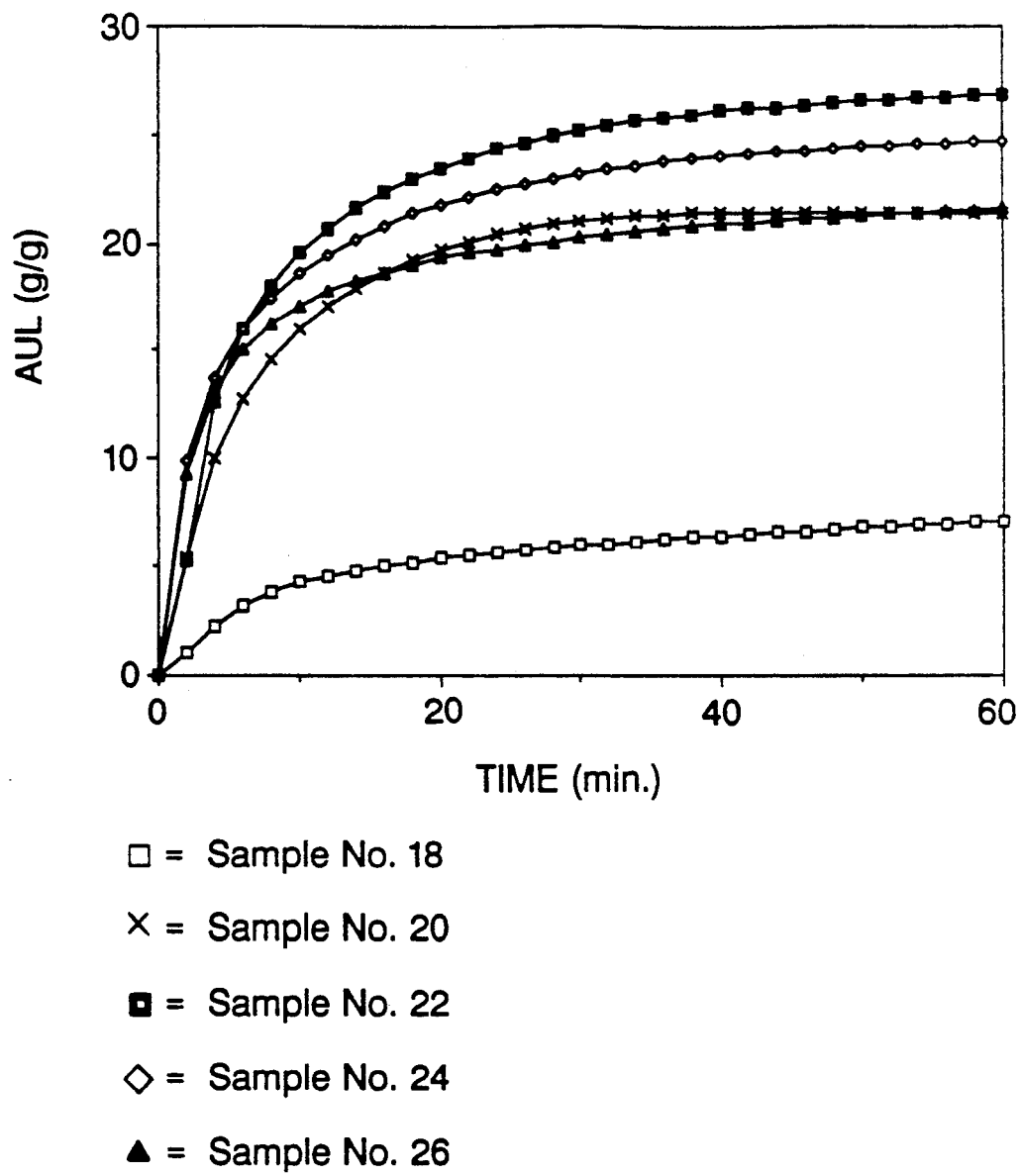
FIG. 2 illustrates the Absorbency Under Load of the carboxymethyl cellulose of Example 1 heat-treated at a temperature of 150° C. for various lengths of time.

FIG. 2 illustrates the Absorbency Under Load of the carboxymethyl cellulose of Example 1 heat-treated at a temperature of 150° C. for various lengths of time. It is noted that the optimum heat-treatment time appears to be approximately 45 minutes, producing an absorbent carboxymethyl cellulose having an Absorbency Under Load of about 27.

Figure 3:
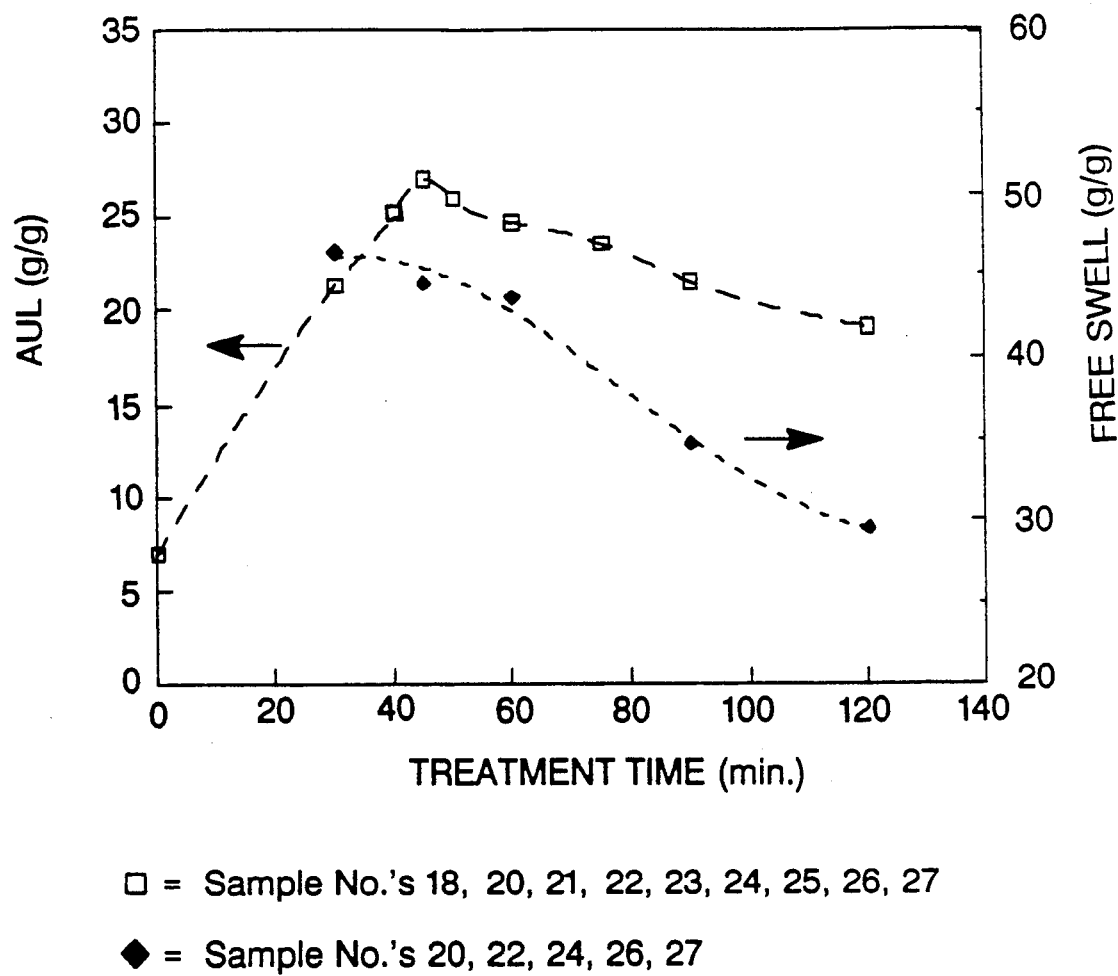
FIG. 3 illustrates the effect of time of heat-treatment on Absorbency Under Load values and Free-Swell Capacity.

FIG. 3 illustrates the effect of time of heat-treatment on Absorbency Under Load values and Free-Swell Capacity as a function of treatment time at 150° C. As can be seen from reference to FIG. 3, an optimum treatment time can be determined.

Figure 4:
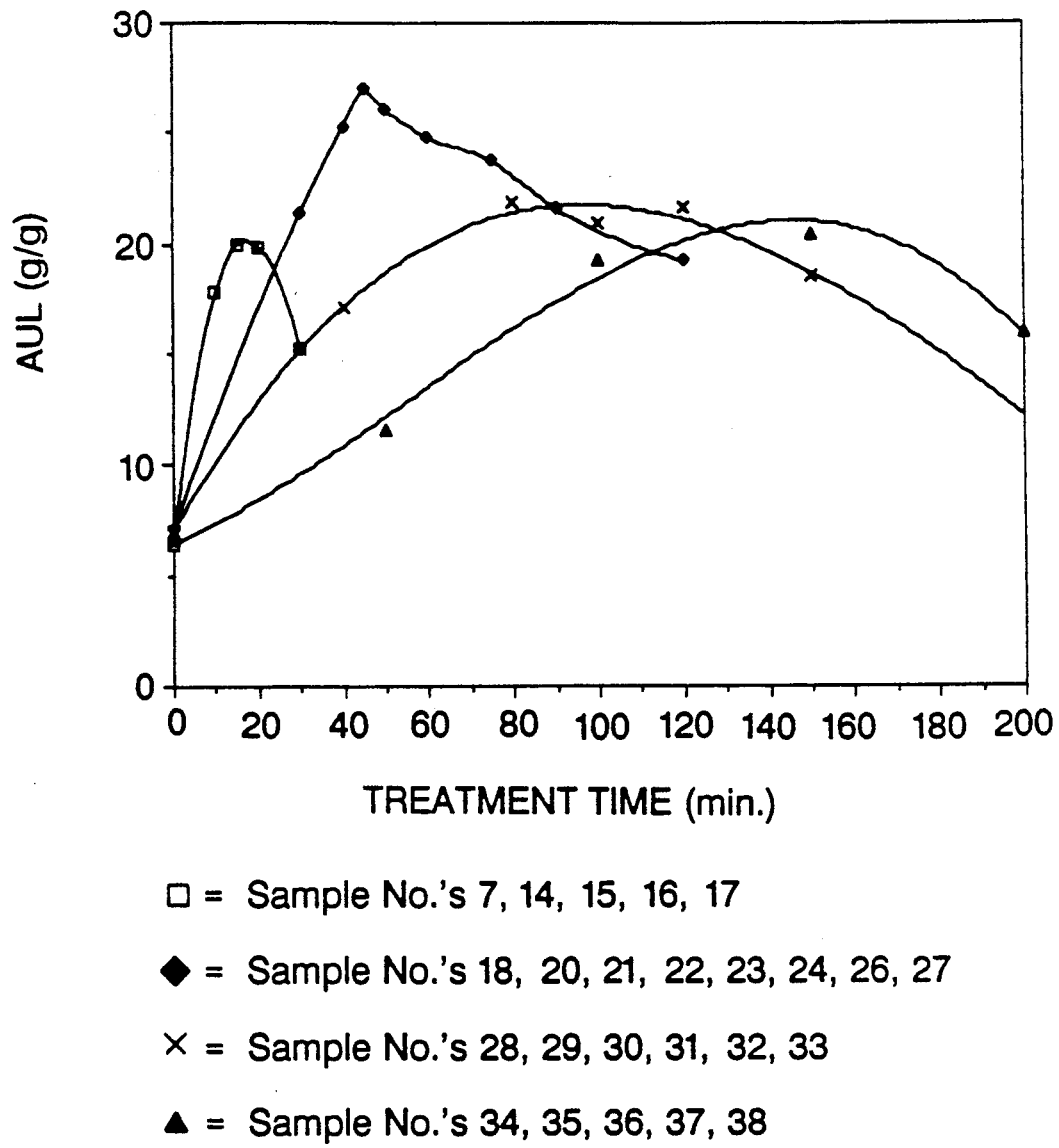
FIG. 4 illustrates the effect of the initial solution pH on the Absorbency Under Load of carboxymethyl celluloses treated at 150° C. for various lengths of time.

FIG. 4 illustrates the effect of the initial pH of the solution of carboxymethyl cellulose and water on the Absorbency Under Load of carboxymethyl celluloses treated at 150 C for various periods of time. As can be seen from reference to FIG. 4, varying the initial pH of the solution of carboxymethyl cellulose and water alters the optimum treatment time. As a general rule, the lower the pH, the shorter the treatment time to optimize absorbent properties.

Figure 5:
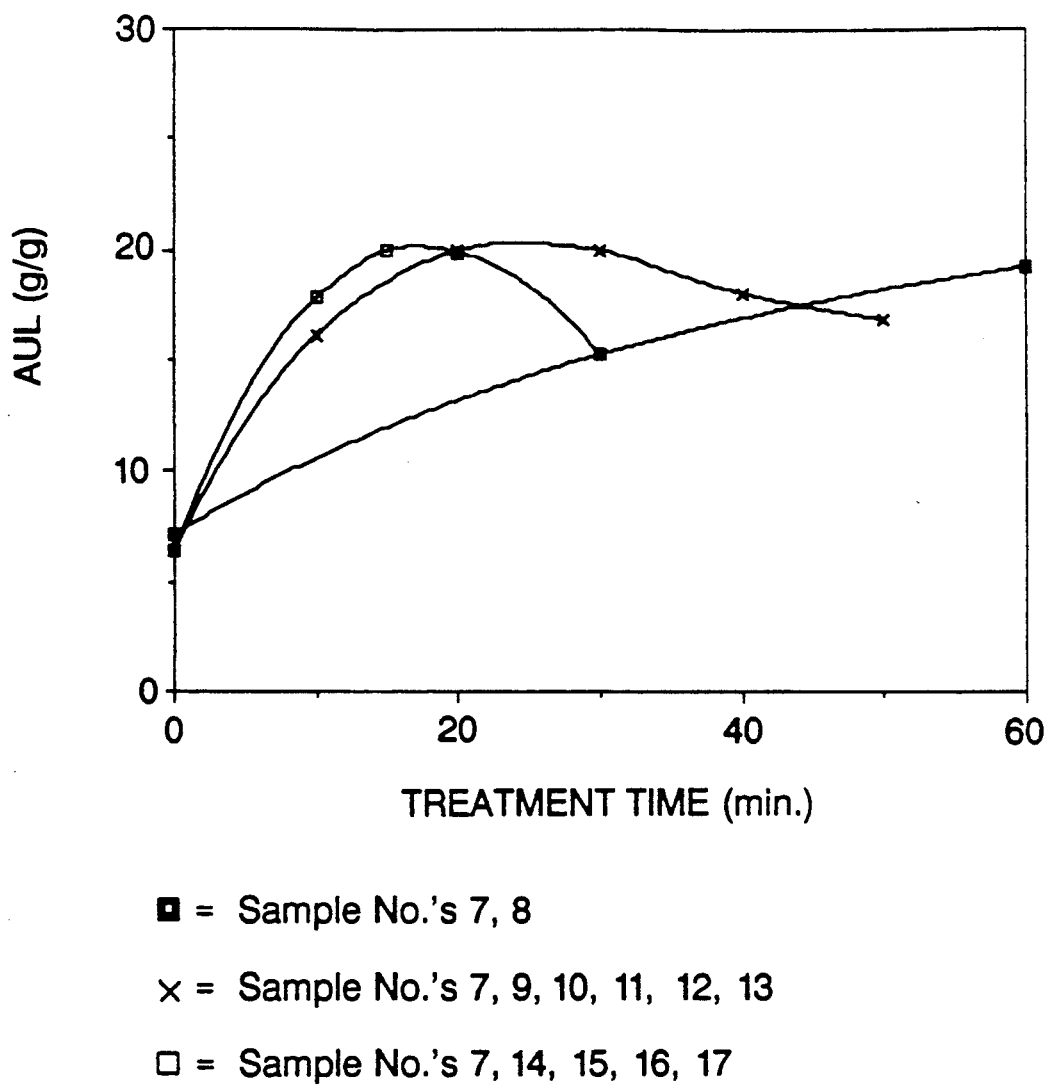
FIG. 5 illustrates the effect of temperature of heat-treatment on the Absorbency Under Load values of carboxymethyl cellulose of a slightly acidified system.

FIG. 5 shows the effect of temperature of heat-treatment on the Absorbency Under Load values of carboxymethyl cellulose of a slightly acidified system (0.5 DA). As can be seen from reference to FIG. 5, the higher the treatment temperature, the shorter the time necessary to obtain the optimum Absorbency Under Load value.

Figure 6:
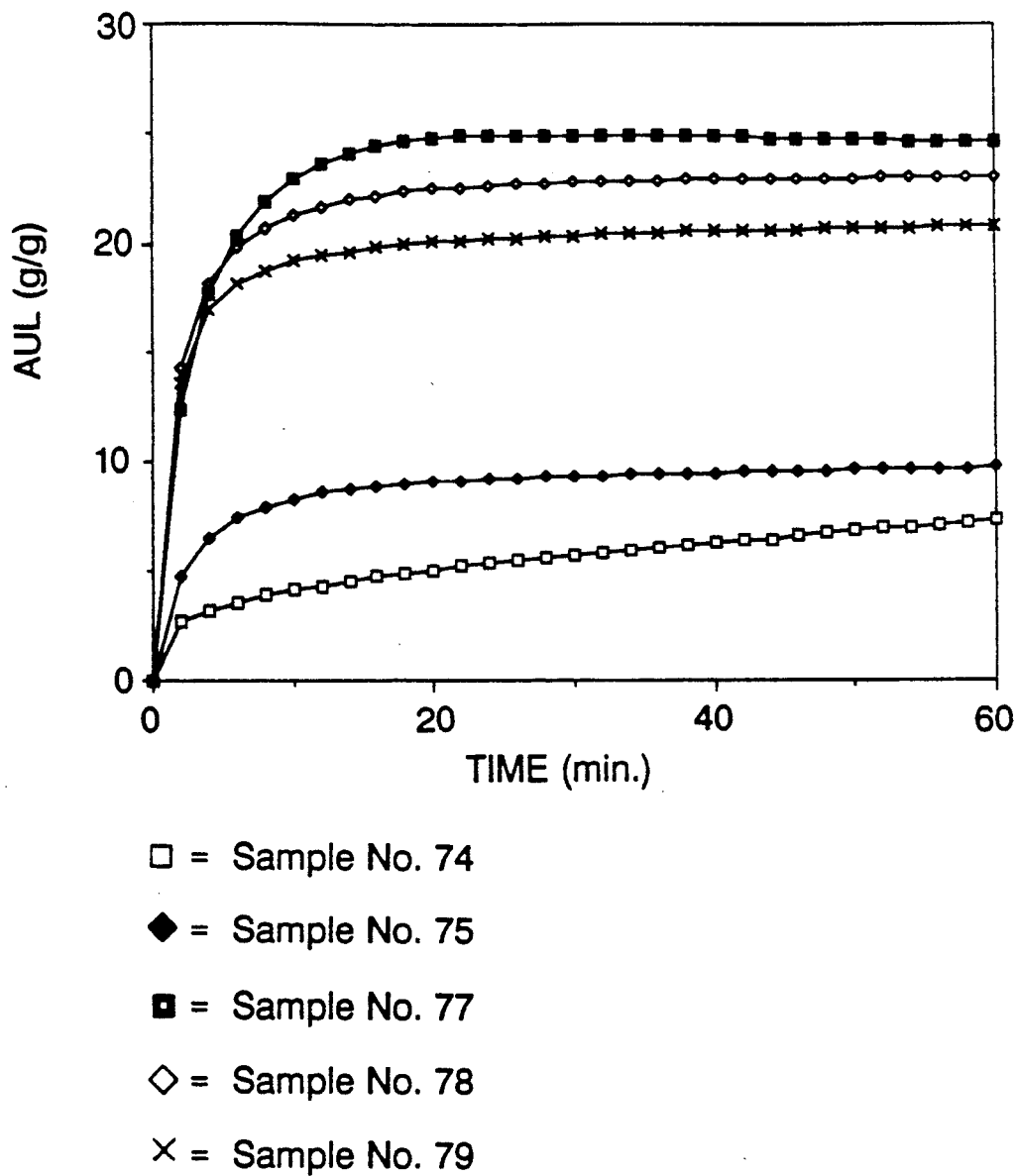
FIG. 6 illustrates the Absorbency Under Load value of the carboxymethyl cellulose of Example 3 heat-treated at 150° C. for various times.

FIG. 6 illustrates the Absorbency Under Load value of the carboxymethyl cellulose of Example 3 heat-treated at 150° C. for various times. Again, as can be seen from reference to FIG. 6, an optimum heat-treatment time can be determined. In the case of FIG. 6, the optimum time is about 20 minutes.

Figure 7:
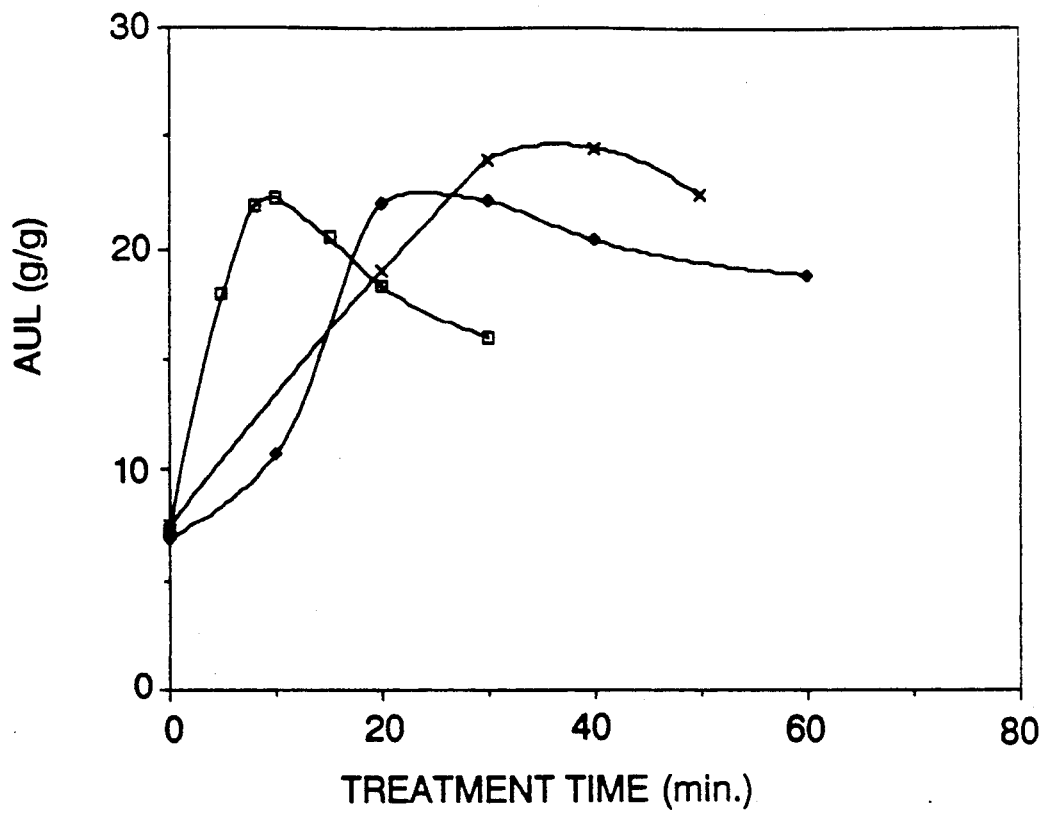
FIG. 7 illustrates the effect of the degree of molar acidification on the carboxymethyl cellulose of Examples 2 and 3.

FIG. 7 illustrates the effect of the degree of molar acidification on the carboxymethyl cellulose of Examples 2 and 3. As can be seen from reference to FIG. 7, the more acidic the carboxymethyl cellulose, the shorter the time necessary to achieve the optimum Absorbency Under Load value.

Figure 8:
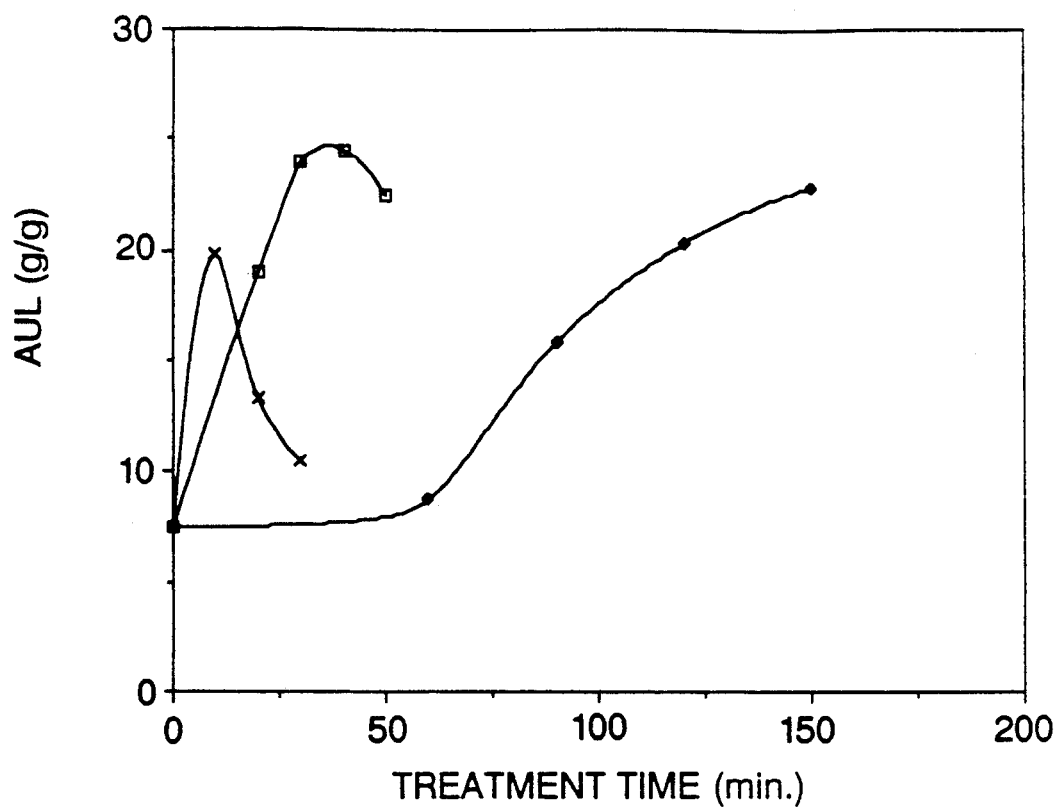
FIG. 8 illustrates the effect of temperature of the heat-treatment process on the Absorbency Under Load performance of the carboxymethyl cellulose of Examples 2 and 3.

FIG. 8 illustrates the effect of temperature of the heat-treatment process on the Absorbency Under Load performance of the carboxymethyl cellulose of Examples 2 and 3. Again, it is seen that as the temperature of heat-treatment increases, the time necessary to achieve to the optimum Absorbency Under Load value decreases.

Figure 9:
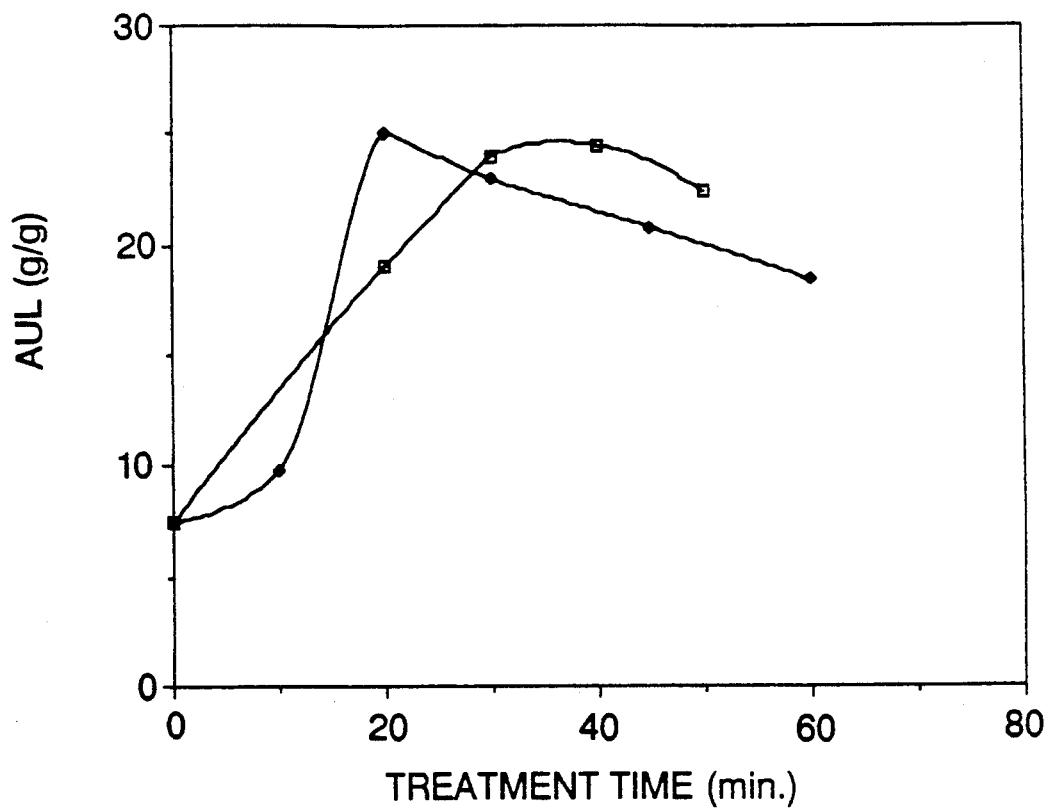
FIG. 9 illustrates the effect of the geometry of the carboxymethyl cellulose on the Absorbency Under Load performance.

FIG. 9 illustrates the effect of the geometry of the carboxymethyl cellulose on the Absorbency Under Load performance. As can be seen from reference to FIG. 9, carboxymethyl cellulose in the form of flakes tends to reach the optimum Absorbency Under Load value faster.

Figure 10:
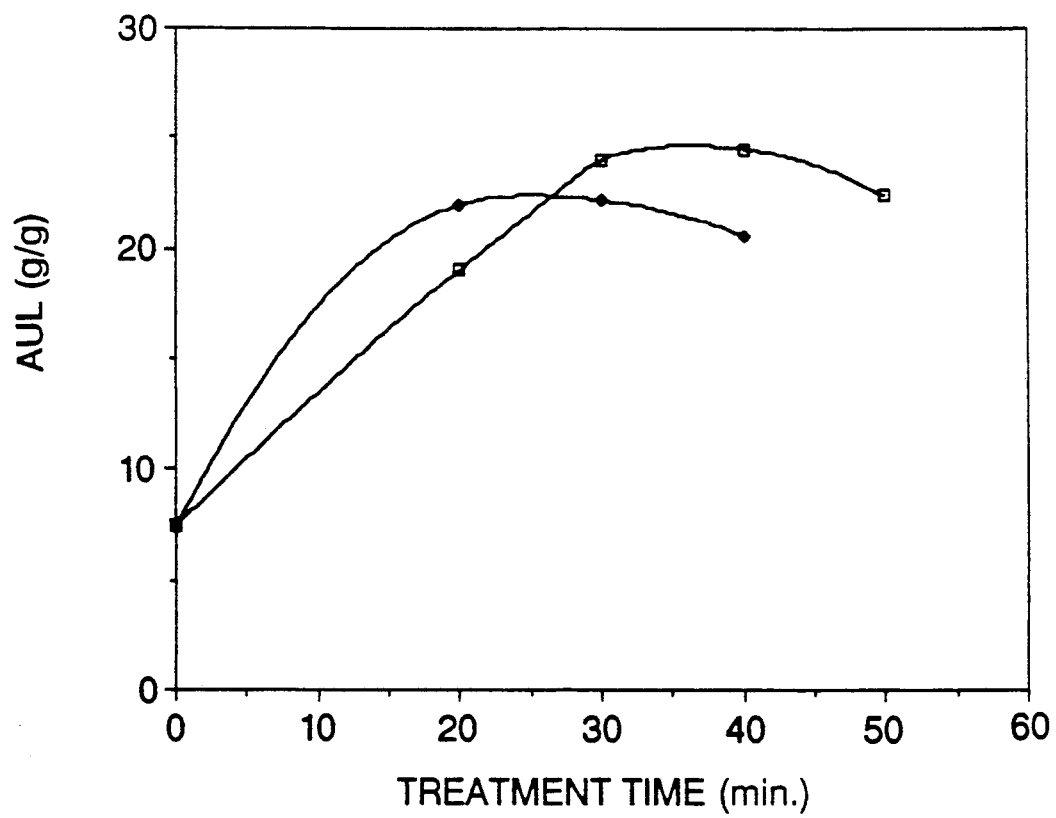
FIG. 10 illustrates the effect of the concentration of carboxymethyl cellulose in the initial solution of carboxymethyl cellulose and water.

FIG. 10 illustrates the effect of the concentration of carboxymethyl cellulose in the initial solution of carboxymethyl cellulose and water. Reference to FIG. 10 shows that, at higher concentrations of carboxymethyl cellulose, lower maximum Absorbency Under Load values are achieved, but that such values are achieved faster than at lower concentrations.

While the present invention has been described in terms of the specific embodiments described above, numerous equivalent changes and modifications will be clear to those skilled in the art. Accordingly, the specific examples set forth above are not intended to limit, in any manner, the scope of the invention as set forth in the appended claims.

What is claimed is:

1. A method for producing a water-swellable, water-insoluble carboxyalkyl polysaccharide, said method comprising the following steps:
   forming a solution comprising a water-soluble carboxyalkyl polysaccharide and water, said carboxyalkyl polysaccharide having an average degree of substitution from about 0.3 to about 1.5;
   recovering said carboxyalkyl polysaccharide from said solution; and
   heat-treating said recovered carboxyalkyl polysaccharide at a temperature and for a time sufficient to crosslink said carboxyalkylpolysaccharide to render said carboxyalkyl polysaccharide generally water insoluble.

2. The method according to claim 1 wherein the carboxyalkyl polysaccharide is a carboxyalkyl cellulose.

3. The method according to claim 2, wherein the solution comprises from about 0.01 to about 90 weight percent of said carboxyalkyl cellulose.

4. The method according to claim 2, wherein said carboxyalkyl cellulose has a degree of substitution of from about 0.4 to about 1.2.

5. The method according to claim 1, wherein said solution comprising said carboxyalkyl polysaccharide and water has a degree of acidification of less than 0.07.

6. The method according to claim 1, wherein said solution comprising said carboxyalkyl polysaccharide and water has a generally neutral pH.

7. The method according to claim 2, wherein said carboxyalkyl cellulose is carboxymethyl cellulose.

8. The method according to claim 1, wherein said carboxyalkyl polysaccharide is recovered from said solution by evaporative drying.

9. The method according to claim 1, wherein said carboxyalkyl polysaccharide is recovered from said solution by precipitation.

10. The method according to claim 2, wherein said recovered carboxyalkyl cellulose is heat-treated at a temperature and for a time sufficient to provide said carboxyalkyl cellulose with an Absorbency Under Load of at least about 17.

11. The method according to claim 2, wherein said recovered carboxyalkyl cellulose is heat-treated at a temperature and for a time sufficient to provide said carboxyalkyl cellulose with an Absorbency Under Load of at least about 24.

12. The method according to claim 2, wherein said recovered carboxyalkyl cellulose is heat-treated at a temperature and for a time sufficient to provide said carboxyalkyl cellulose with an Absorbency Under Load of at least about 27.

13. The method according to claim 10, wherein said carboxyalkyl cellulose is heat-treated at a temperature of from about 120° C. to about 200° C. for a time of from about 1 minute to about 120 minutes.

14. The method according to claim 13, wherein said carboxyalkyl cellulose is heat-treated at a temperature of from about 130° C. to about 170° C. for a time of from about 1 minute to about 120 minutes.

15. The method according to claim 14, wherein said carboxyalkyl cellulose is heat-treated at a temperature of from about 130° C. to about 170° C. for a time of from about 5 minutes to about 60 minutes.

16. The method according to claim 1, further comprising the step of comminuting said carboxyalkyl polysaccharide after recovery and before heat-treating.

17. A method for producing a water-swellable, generally water-insoluble carboxyalkyl polysaccharide, said method comprising the following sequential steps:
   forming a solution comprising from about 0.01 to about 90 weight percent of a water-soluble carboxyalkyl polysaccharide, based on total solution weight and water, said carboxyalkyl polysaccharide having an average degree of substitution of from about 0.4 to about 1.2;
   recovering said carboxyalkyl polysaccharide from said solution; and
   heat-treating said recovered carboxyalkyl polysaccharide at a temperature of from about 100° C. to about 250° C. for a time of from about 1 minute to about 600 minutes, such that said carboxyalkyl polysaccharide is rendered generally water-insoluble and has an Absorbency Under Load of at least about 17.

18. The method according to claim 17 wherein the carboxyalkyl polysaccharide is a carboxyalkyl cellulose.

19. A carboxyalkyl polysaccharide produced by the method of claim 1.

20. A carboxyalkyl polysaccharide produced by the method of claim 17.

21. A carboxyalkyl cellulose produced by the method of claim 18.

22. A water-swellable, generally water-insoluble, carboxyalkyl polysaccharide characterized in that said carboxyalkyl polysaccharide has an average degree of substitution from about 0.3 to about 1.5 and has an Absorbency Under Load of at least about 17 and a Free-Swell Capacity of at least about 20.

23. The carboxyalkyl polysaccharide according to claim 22, wherein said carboxyalkyl polysaccharide has an Absorbency Under Load of at least about 20.

24. The carboxyalkyl polysaccharide according to claim 22, wherein said carboxyalkyl polysaccharide has an Absorbency Under Load of at least about 24.

25. The carboxyalkyl polysaccharide according to claim 22, wherein said carboxyalkyl polysaccharide has an Absorbency Under Load of at least about 27.

26. The carboxyalkyl polysaccharide according to claim 22, wherein said carboxyalkyl polysaccharide has a Degree of Molar Acidification of less than 0.07.

27. The carboxyalkyl polysaccharide according to claim 22, wherein said carboxyalkyl polysaccharide is generally neutral.

28. The carboxyalkyl polysaccharide according to claim 22, wherein said carboxyalkyl polysaccharide is carboxyalkyl cellulose.

29. The carboxyalkyl cellulose according to claim 28, wherein said carboxyalkyl cellulose is carboxymethyl cellulose.

30. The carboxyalkyl polysaccharide according to claim 25, wherein said carboxyalkyl polysaccharide is carboxymethyl cellulose.

31. The carboxyalkyl cellulose according to claim 28, wherein said carboxyalkyl cellulose has a Free-Swell Capacity of at least about 30.

32. The carboxyalkyl Cellulose according to claim 28, wherein said carboxyalkyl cellulose has a Free-Swell Capacity of at least about 35.

33. The carboxyalkyl polysaccharide according to claim 22, wherein said carboxyalkyl polysaccharide is in the form of discrete particles.

34. A water-swellable, generally water-insoluble, carboxyalkyl polysaccharide characterized in that said carboxyalkyl polysaccharide has an average degree of substitution from about 0.4 to about 1.2 and has an Absorbency Under Load of at least about 20 and a Free-Swell Capacity of at least about 20.

* * * * *